(12) United States Patent
Keane

(10) Patent No.: US 12,023,131 B2
(45) Date of Patent: Jul. 2, 2024

(54) GUIDEWIRE APPARATUS AND METHOD FOR MULTIPLE PARAMETER ANALYSIS OF CORONARY STENOSIS

(71) Applicant: CARDIOWIRE LIMITED, Sandyford (IE)

(72) Inventor: David Keane, Dublin (IE)

(73) Assignee: CARDIOWIRE LIMITED, Dublin (IE)

(*) Notice: Subject to any disclaimer, the term of this patent is extended or adjusted under 35 U.S.C. 154(b) by 875 days.

(21) Appl. No.: 17/091,463

(22) Filed: Nov. 6, 2020

(65) Prior Publication Data
US 2021/0161396 A1 Jun. 3, 2021

Related U.S. Application Data

(63) Continuation of application No. 15/597,907, filed on May 17, 2017, now abandoned.

(60) Provisional application No. 62/338,825, filed on May 19, 2016.

(51) Int. Cl.
*A61B 5/00* (2006.01)
*A61B 5/02* (2006.01)
(Continued)

(52) U.S. Cl.
CPC ........ *A61B 5/02007* (2013.01); *A61B 5/0245* (2013.01); *A61B 5/0538* (2013.01);
(Continued)

(58) Field of Classification Search
CPC .......... A61M 2025/0166; A61M 25/01; A61B 5/0538; A61B 5/1076; A61B 5/02007; A61B 2017/00026; A61B 5/053; A61B 5/287; A61B 18/1492; A61B 2562/043; A61B 5/026; A61B 5/283; A61B 5/068; A61B 5/30; A61B 5/6852; A61B 5/0535; A61B 5/489; A61B 5/6851; A61B 5/7271;
(Continued)

(56) References Cited

U.S. PATENT DOCUMENTS

| 4,587,975 A | 5/1986 | Salo et al. |
| 5,514,171 A * | 5/1996 | Hoegnelid ............... A61B 5/03 607/122 |

(Continued)

FOREIGN PATENT DOCUMENTS

| JP | 2012502773 A | 2/2012 |
| WO | 2013055896 A1 | 4/2013 |

*Primary Examiner* — Joseph A Stoklosa
*Assistant Examiner* — Brian M Antiskay
(74) *Attorney, Agent, or Firm* — Mintz Levin Cohn Ferris Glovsky and Popeo, P.C.

(57) ABSTRACT

A Percutaneous Coronary Intervention (PCI) guidewire and method of use includes at least two pairs of small surface area, closely spaced electrodes spaced axially along the length of the guidewire to allow one electrode pair to be positioned on each side of a coronary stenosis. The electrodes can sense electrical signals from the myocardium immediately adjacent to the electrodes, enabling the guidewire to record and analyze an Intra-Coronary Electrogram (ICEG) and heart pacing, and, therefore, facilitate more accurately diagnosis of an individual patient's stenosis and provide a more patient specific diagnosis of clinical need.

14 Claims, 11 Drawing Sheets

(51) Int. Cl.
    *A61B 5/0245*     (2006.01)
    *A61B 5/05*     (2021.01)
    *A61B 5/0538*     (2021.01)
    *A61B 5/287*     (2021.01)

(52) U.S. Cl.
    CPC ............ *A61B 5/287* (2021.01); *A61B 5/6851* (2013.01); *A61B 5/6852* (2013.01); *A61B 5/7257* (2013.01); *A61B 5/7289* (2013.01)

(58) Field of Classification Search
    CPC ........ A61B 6/5211; A61B 2017/00053; A61B 2018/00351; A61B 2018/00744; A61B 2018/00892; A61B 2090/065; A61B 5/027; A61B 2018/00363
    USPC ........ 600/372–375, 377, 381, 442, 506–507, 600/547
See application file for complete search history.

(56) References Cited

U.S. PATENT DOCUMENTS

| | | |
|---|---|---|
| 5,967,978 A | 10/1999 | Littmann et al. |
| 2009/0062684 A1 | 3/2009 | Gregersen et al. |
| 2009/0143651 A1 | 6/2009 | Kallback et al. |
| 2009/0326397 A1* | 12/2009 | Behzadi ................... A61B 5/05 600/508 |
| 2010/0010312 A1 | 1/2010 | Gilad et al. |
| 2010/0210958 A1 | 8/2010 | Manwaring et al. |
| 2011/0306867 A1 | 12/2011 | Gopinathan et al. |
| 2012/0078342 A1 | 3/2012 | Vollkron et al. |
| 2013/0096409 A1 | 4/2013 | Hiltner et al. |
| 2014/0228684 A1 | 8/2014 | Kassab |
| 2014/0316289 A1 | 10/2014 | Kassab |
| 2015/0012007 A1 | 1/2015 | Arevalos |
| 2015/0289931 A1 | 10/2015 | Puryear et al. |
| 2017/0065223 A1 | 3/2017 | Razavi et al. |

* cited by examiner

GUIDEWIRE APPARATUS AND METHOD FOR MULTIPLE PARAMETER ANALYSIS OF CORONARY STENOSIS

FIELD OF THE INVENTION

The disclosure relates to coronary artery disease, and, more specifically, to an apparatus and technique for assessing the clinical need for stenting a stenotic coronary artery.

BACKGROUND

Coronary artery disease is characterized by stenosis (narrowing) of one or more coronary arteries of a patient. Traditional noninvasive cardiology practice involves opening or removal of such stenosis, typically through Percutaneous Coronary Intervention (PCI) by balloon inflation angioplasty) stenting at the site of the former stenosis. Recent studies have shown that stenting clinically inconsequential coronary stenoses places patients at risk for complications associated with the procedure and subsequent stent occlusion due to thrombosis. Angiography has traditionally been used as a diagnostic tool to determine the need for a stent. Contrast angiography is subjective and based on the physician's individual judgment. More recently Fractional Flow Reserve (FFR) studies which measures the hemodynamic pressure drop associated with a coronary stenosis, has been utilized to determine the severity of a coronary stenosis. However, these techniques utilize measurement of only a single parameter and may provide insufficient information for patients with borderline clinical needs, multi-vessel disease, or no clinical need.

Accordingly, need exists for an apparatus and technique which can provide multiple assessments of an individual coronary stenosis and its subtended myocardium to provide additional clinical data to evaluate patients with borderline indications, specific stenosis in patients with multi-vessel disease, and patients with no clinical need.

SUMMARY

Disclosed is a Percutaneous Coronary Intervention (PCI) guidewire with multiple electrode pairs enabling the guidewire to record an Intra-Coronary Electrogram (ICEG) and heart pacing, and, therefore, facilitate more accurate diagnosis of an individual patient's stenosis and provide a more patient specific diagnosis of clinical need. The disclosed apparatus and technique enable detection of ischemia and the viability of the subtended myocardium, neither of which are provided by FFR techniques. The apparatus, system and techniques disclosed herein can provide multiple assessments of an individual coronary stenosis and its subtended myocardium, as explained herein.

According to one aspect of the disclosure, a guidewire comprises an elongate tubular body having a core wire extending therethrough to a tip at a distal end thereof. The distal end of the guidewire further comprises two pairs of small surface area, closely spaced electrodes electrically couplable to a current source at the proximal end of the guidewire. Electrodes can sense electrical signals from the myocardium immediately adjacent to the electrodes. The electrode pairs are spaced axially along the length of the guidewire to allow one electric pair to be positioned on either side of a coronary stenosis.

According to another aspect of the disclosure, a method for determining the necessity of performing a PCI or stenting procedure utilizes electrogram analyses, subanalyses, derivatives, rate of change of parameters over the cardiac cycle, and both time and frequency domain FFT (Fast Fourier Transform) analyses of signal data collected with the disclosed guidewire to determine the necessity of stenting a stenosis.

According to another aspect of the disclosure, a method for determining the necessity of performing a PCI or stenting procedure comprises: A) positioning a pair of electrodes within a vessel on both sides of a stenosis; B) measuring with a measurement circuit electrically coupled to the electrodes the impedance within the vessel across the stenosis, and C) comparing the measured impedance with one of a predetermined impedance value or a prior impedance measurement.

DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

A stenosis is a narrowing in a vessel which can range from mild, e.g. 20% vessel diameter stenosis to 100% vessel diameter stenosis. An occlusion is a blockage, e.g. 100% stenosis, and is easy to quantify and see on coronary angiography. An electrocardiogram (EKG/ECG) is a recording of the electrical signal from the whole heart from the body surface. Conventionally the term electrogram is used to describe a local signal recording from a single point of the heart. Conventional EP studies record Endocardial electrograms. With the disclosed guidewire, recording an IntraCoronary Electrogram (ICEG) is unique and looks at local epicardial and intramyocardial signals.

Figure 1B:
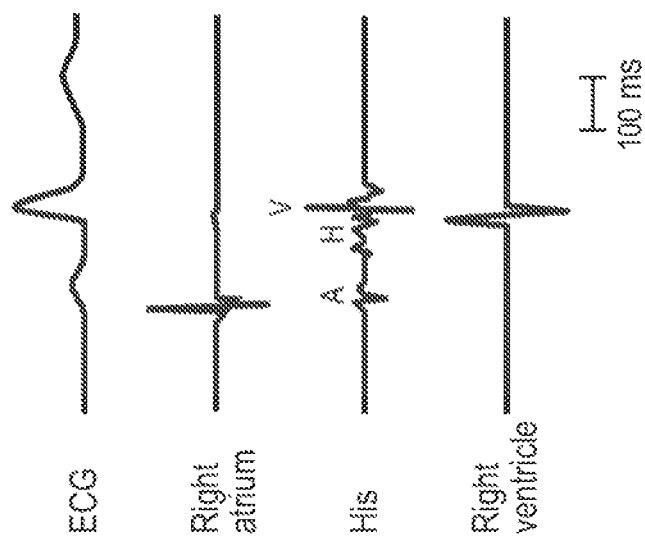
FIG. 1B illustrates conceptually the shape of the electrical signals which collectively comprise an Intra-Coronary Electrogram (ICEG)
Figure 1A:
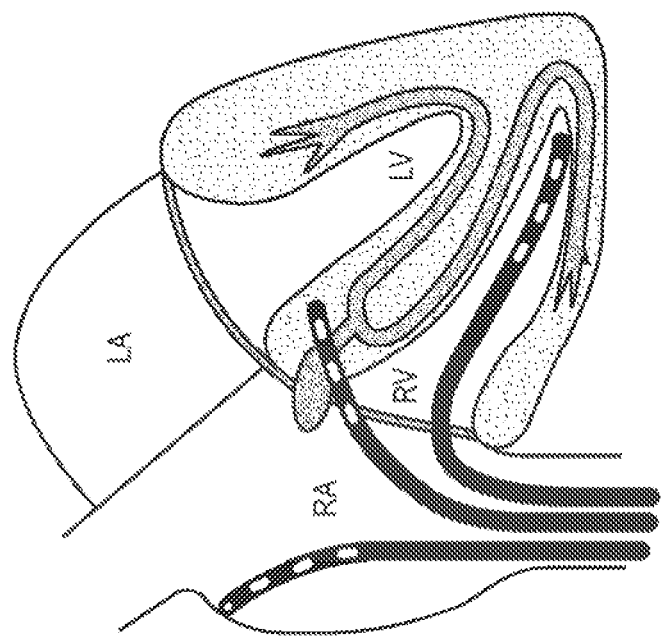
FIG. 1A illustrates conceptually a partial cutaway view of the human heart with electrophysiology catheters placed at various locations therein to map electrical activity.

In the conventional Endocardial Electrophysiology Study (EPS) process, electrophysiology catheters, having a plurality of small, closely spaced exterior electrodes proximate a distal end thereof, are used to map electrical activity as it moves through the heart, as illustrated in FIG. 1A. In the electrophysiology catheter of FIG. 1A, the smaller the separation of the recording electrodes, the more focused the electrogram is on a specific area of electrical activity.

In FIG. 1B, the ECG signal is a classic surface electrogram signal. The right atrium is the signal recorded by the right atrial lead and represents a measurement of right atrial activity. The His is the signal recorded by the His electrode and represents a measurement of the small right atrium, AV node and right ventricle signals. The right ventricular is the signal recorded by the right ventricular electrode and represents a measurement of only the right ventricular activity. Collectively, these internal heart signals comprise Endocardial Electrograms.

Figure 2:
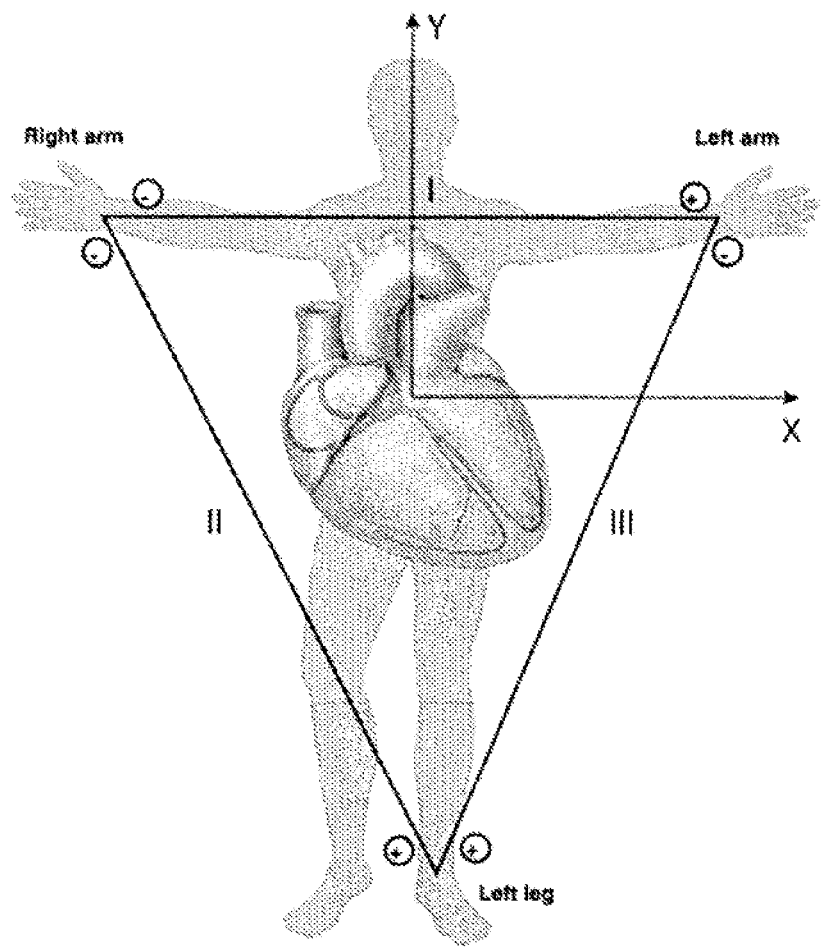
FIG. 2 illustrates conceptually the placement configuration for three lead electrodes for recording an Electrocardiogram.
Figure 3:
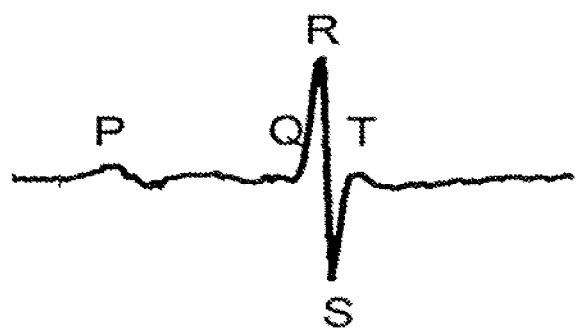
FIG. 3 illustrates conceptually the shape of the electrical signal generated by the heart (electrocardiogram)

FIG. 2 illustrates conceptually the three lead electrode placement for recording the entire cardiac electrogram of the patient. FIG. 3 illustrates conceptually a classic whole heart electrogram, termed an electrocardiogram or EKG, produced by a three lead body surface recording. The shape of the electrical signal generated by the heart, as recorded as an electrogram, is dependent on the location and separation of the electrodes that are used for the recording. A three lead electrocardiogram has large separation, creating a large antenna, and produces the classic whole heart electrocardiogram.

Figure 4A:
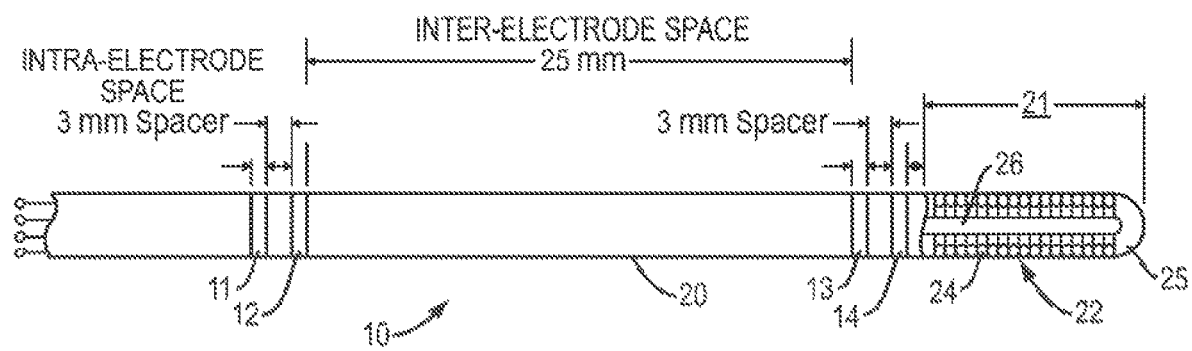
FIG. 4A illustrates conceptually a partial cutaway view of a guidewire in accordance with the disclosure.

FIG. 4 illustrates conceptually a partial cutaway view of a guidewire 10 in accordance with the disclosure. In an illustrative embodiment, the guidewire may have design aspects similar to other commercially available PCI guidewires but with at least two pairs of small surface area, closely spaced, electrodes disposed towards the distal end of the guidewire that can pace and sense the cardiac tissue immediately adjacent to the electrodes. These electrode pairs 11, 12 and 13, 14 are spaced apart axially along a length of the guidewire 10 to allow one pair of electrodes to be positioned on either side of most coronary stenoses. The closer the intra-electrode distance, e.g., the distance between the two electrodes in a pair of electrodes, and the smaller the electrode size, the higher the resultant fidelity of the electrogram, and, the greater the desirable near field signal versus the undesirable far field signal. In embodiments, without being limiting, the individual electrodes may have a width of approximately 0.5 mm and an intra-electrode distance for a given pair of approximately 4 mm between individual electrodes within the same pair. In embodiments, without being limiting, the different pairs of electrodes may be separated, i.e. the interelectrode distance, by approximately 4 cm. Other spatial dimensions between electrodes in a pair, and between different pairs of electrodes may be utilized. In embodiments, the ratio of inter-electrode spacing to intra-electrode spacing may be in the range between 5:1 to 40:1, or more specifically between 7:1 to 25:1, or even more specifically between 12:1 to 18:1. Each of the electrodes of electrode pairs 11, 12 and 13, 14 are coupled to electrically conductive leads which extend proximally through the guidewire 10 and are electrically couplable to signal source 15 and measurement circuit 16 which receive and process the signals from electrode pairs 11, 12 and 13, 14 in the manner described herein.

The electrode pairs may be formed of any biocompatible electrically conductive material as can the electrical leads extending proximally along the axial length of the guidewire and connectable to a signal source and measurement circuit module 16. In one embodiment, the electrode pairs and their respective leads may be designed for from MRI compatability, e.g. gold electrodes and copper wire leads or carbon and/or plastics conductive materials.

Guidewire 10 includes an elongate cylindrical tube 20 of semi-rigid material, such as a natural or synthetic resin, having enough columnar strength to allow it to be advanced through tortuous vasculature but flexible enough to negotiate curves within the vasculature. The guidewire exterior, particularly the distal end region 21 may have a polymer covered distal tip 22. The distal end of the guidewire 10 may be implemented with a helical platinum coil 24 coupled to a hemispherical bead tip 25, as illustrated in FIG. 4. A core wire 26 extends through the interior length of the guidewire 10 and may have a cross-sectional diameter which narrows distally in either a stepped or progressively tapered manner. The core wire 26 may be coupled to one or both of the helical coil 24 or bead tip 25 to facilitate torqueing and steering of the guidewire 10. In one embodiment, the distal end region 21 of the guidewire 10 may be manually bendable or shapeable to retain a manually created curve, as in standard coronary guide wires. In another embodiment the distal tip 22 of the guidewire may be manually deflectable with an operator's handle from the proximal end of the guidewire in a manner understood from current commercially available steerable guide wires. In embodiments, the material from which the electrodes and/or guidewire tip are made may have increased radio-opacity for visual detection during placement of the guidewire. In embodiments, a portion of the guidewire, typically the distal tip region, may be made of a shape memory metal which reverts to a predetermined shape once reaching a threshold temperature within a patient vessel.

Proximal electrode pair 11, 12 and distal electrode pair 13, 14 may be carried on the exterior surface of cylindrical tube 20, either on the exterior diameter thereof or seated in indentations in the surface of tube 20, and are electrically coupled to leads which extend proximally through guidewire 10 for electrical coupling with the interface of measurement circuit module 16. Such electrical leads will be typically insulated and may extend through the hollow interior of 20 or may be embedded in the wall thereof. The source of a current signal may also be included within measurement circuit module 16. Note, in embodiments, the individual electrodes 11, 12, 13, 14 may be coupled to a signal generator as well as measurement circuit module 16 in any configuration become as appropriate or in selectable configurations, e.g. electrode pairs electrically coupled in series with a signal generator or measurement circuit module 16, all electrodes in parallel with a signal generator or measurement circuit module 16, electrode pairs in parallel with a signal generator or measurement circuit module 16, or other configurations.

Figure 10A:
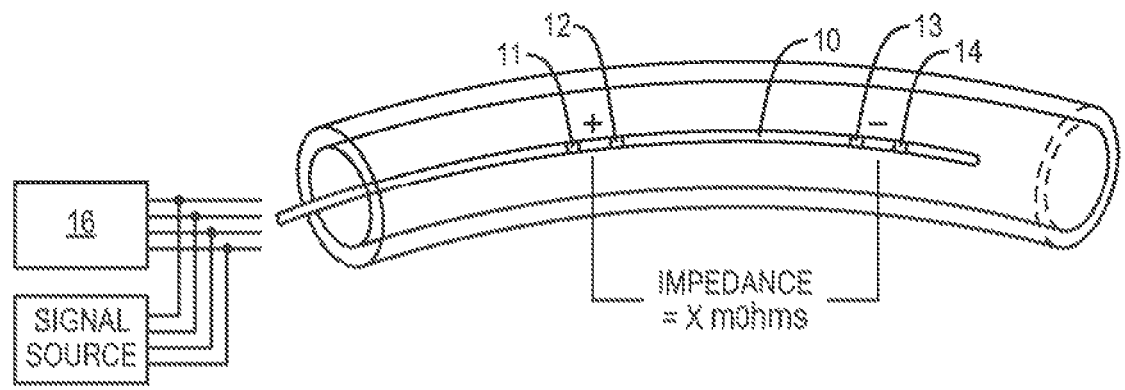
FIG. 10A illustrates conceptually the placement of the disclosed guidewire relative to a normal coronary artery.
Figure 11B:
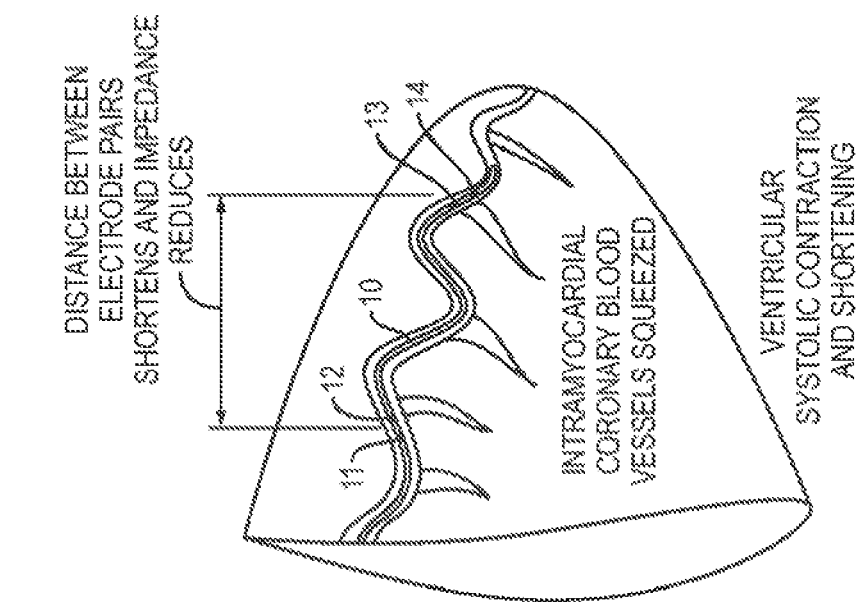
FIG. 11B illustrates conceptually the placement of the disclosed guidewire relative to a normal coronary artery ventricular systolic contraction in accordance with the disclosure.
Figure 11A:
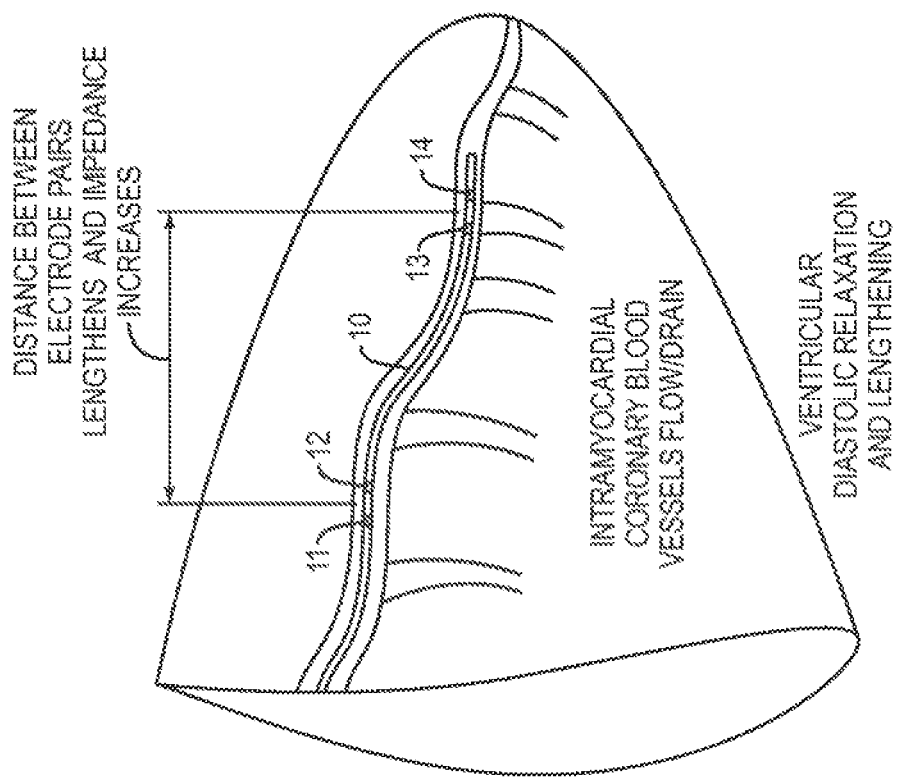
FIG. 11A illustrates conceptually the placement of the disclosed guidewire relative to a normal coronary artery during ventricular diastolic relaxation in accordance with the disclosure.

In practice, the guidewire 10 is connected to a signal source and measurement circuit module 16 and is inserted through a coronary guiding catheter percutaneously inserted into the body, typically through the radial or femoral artery, and positioned with the help of a fluoroscopic imaging system across an intracoronary stenosis with one pair of electrodes positioned on each side of the stenosis. The impedance across the stenosis within the vessel between the distal electrode pair and proximal electrode pair is then measured by measurement circuit module 16. Note that the shape and length of the coronary artery at issue may vary during ventricular relaxation and contraction. Because the distance between electrode pairs lengthens during ventricular diastolic relaxation and lengthening, causing an impedance increase, as illustrated in FIG. 11A, and the distance between electrode pairs shortens during ventricular systolic contraction and shortening causing an impedance decrease, as illustrated in FIG. 11B, the step of measuring impedance with the disclosed guidewire across a coronary stenosis or occlusion may be taken multiple times to achieve an averaged impedance value. Such averaged impedance value may be then compared with an empirically derived, predetermined impedance value or a previously measured, averaged impedance value taken with the disclosed guidewire with both pairs of electrodes proximal of the stenosis or occlusion. The difference in the impedance values is then determined and presented to the practitioner as an aid to determining whether or not the difference in impedance values is indicative of a stenosis or occlusion which requires the necessity to perform a PCI or stenting procedure. Such determination may be made on the assumption that an occlusion or stenosis of tighter diameter or higher percentage of coronary obstruction will have a higher impedance value. A measurement of the impedance between the respective pairs of electrodes is taken using measurement circuitry 16 electrically coupled at the proximal end of guidewire to the electrode pairs. As illustrated in FIG. 10A, the impedance of an unobstructed coronary artery is represented by the following equation:

$$\text{Impedance} = X \text{ mOhms}$$

Figure 10B:
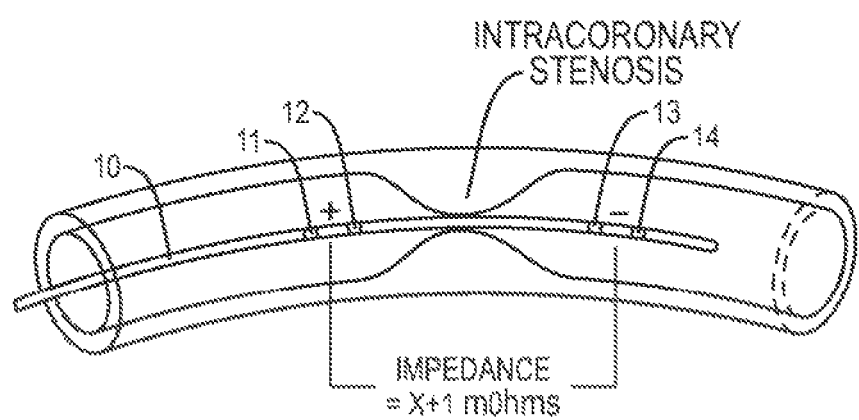
FIG. 10B illustrates conceptually the placement of the disclosed guidewire across an occluded coronary artery.

FIG. 10B, the impedance of an obstructed coronary artery is represented by the following equation:

$$\text{Impedance} = X + 1 \text{ mOhms}$$

Using the disclosed guidewire and techniques, the intracoronary impedance is measured throughout the ECG gaited cardiac cycle. The range of impedance change during the cardiac cycle is then quantified. Any difference reflects lengthening of the interelectrode distance during systole and diastole and local contraction. Subanalyses and derivations of the dynamic change and timing of the changes with respect to the ECG gaited cardiac cycle provide information on the vessel wall compliance. If a segment of a vessel is healthy, the vessel wall will be compliant demonstrating elasticity and increases in diameter during periods of highest intracoronary pressure during the cardiac cycle. If a segment of a vessel has a circumferential hard fibrotic and/or calcified plaque, the segment will be non-compliant and will not demonstrate elasticity (as demonstrated by a change in segment diameter during the cardiac cycle). Through subanalysis of the derivatives of the change, the rate of change and timing of the change in relation to the cardiac cycle, the functional characteristics of a coronary stenosis as well as the functional characteristics of the subtended myocardium, may be determined.

If the subtended myocardium is healthy, the interelectrode distance will change significantly over the cardiac cycle. If the subtended myocardium is ischemic, the motion will be reduced; the more ischemic the more the degree of hypokinesia. If the subtended myocardium is hibernating, it will be akinetic, that is, there will be no significant change in impedance over the cardiac cycle. If the subtended myocardium is non-viable (dead), it will be akinetic. Hibernating (viable) myocardium may be differentiated from non-viable myocardium by analysis of local electrograms. The electrograms from viable hibernating myocardium will have large amplitude, high-frequency (local) signals while non-viable myocardium will have a paucity or absence of high-frequency local signals.

Continuous measurement of electrical impedance throughout ECG gaited cardiac cycle provides information on vessel mechanical compliance. Intracoronary pressure is greatest during cardiac systole (peak driving pressure from the aorta and peak resistance from the compressed intramyocardial distal coronary branches. During ventricular diastole, coronary flow is maximal (as its end vessels are no longer compressed by the myocardial contraction). The vessel diameter of a healthy segment of vessel will vary during the cardiac cycle accordingly. If a diseased segment of the vessel has hard (e.g. calcified) non-compliant circumferential atherosclerotic plaque, all disclosed guidewire and techniques described herein can be utilized to provide information on vessel segment compliance, and, thereby plaque composition and plaque eccentricity/circumferential distribution, beyond that provided by simple non-ECG gaited impedance measurement.

According to another aspect of the disclosure, in a method for determining the necessity of performing a PCI or stenting procedure, measurement circuit module 16 processes signals from the in situ guidewire 10 utilizing any of electrogram analyses, subanalyses, derivatives, rate of change of parameters over the cardiac cycle and both time and frequency domain FFT (Fast Fourier Transform) analyses.

In an illustrative embodiment, measurement circuit module 16 may be single unit or a collection of modules comprising a system that comprises appropriate interface circuitry for coupling to the conductive leads of guidewire 10, measures impedance between pairs of electrodes, optionally provides monitoring of signals from the electrode pairs, and further optionally comprises a computational module which may be implemented with a processor microprocessor based system and accompanying memory or a general-purpose computer having appropriate logic and software for executing appropriate instructions to compute values for parameters including, but are not limited to any of the following:

Depolarization electrogram components
Repolarization electrograms components
Full band width sampling (including high and low frequency components)
Detection and distribution of local electrical Alternans of repolarization components as well as Alternans of depolarization components
Time domain analysis
Frequency domain analysis
Fast Fourier Transform analysis
Degree of fragmentation
Summation as well as individual components Ratios/indices/derivatives of multiple components providing a combined metric Rate of change of (dynamic) components during the (intra) cardiac cycle Rate of change between (inter) cardiac cycles (e.g. when heart rate brought to different rates or ischemia is induced)

Pacing threshold

Pacing latency

Pacing impedance.

In embodiments, the averaged impedance value measured across a stenosis or occlusion may be compared with empirically derived impedance values representing any of an un-occluded coronary artery, a mildly occluded coronary artery, a substantially occluded coronary artery, or a fully occluded coronary artery. In embodiments, based on the results of such comparison, the measurement apparatus may indicate which of the previously empirically derived impedance values the measured average impedance value most closely approximates to assist the practitioner in determining the necessity to perform a PCI or stenting procedure.

Figure 5:
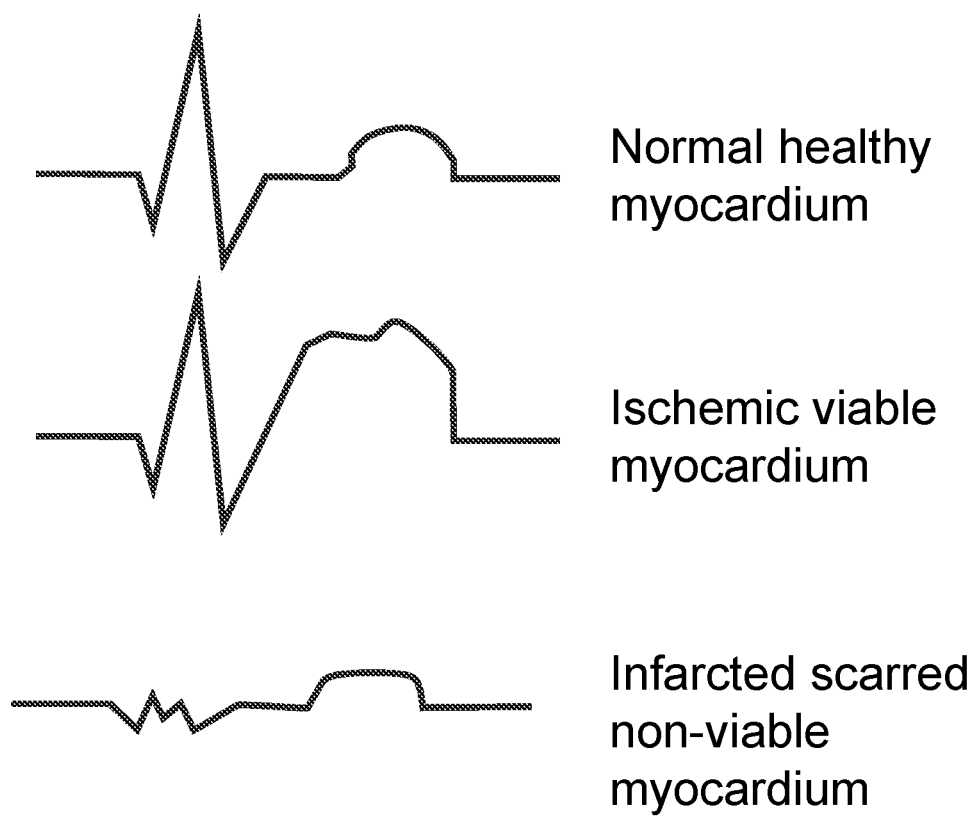
FIG. 5 illustrates conceptually the electrogram characteristics from a subtended myocardium.
Figure 6:
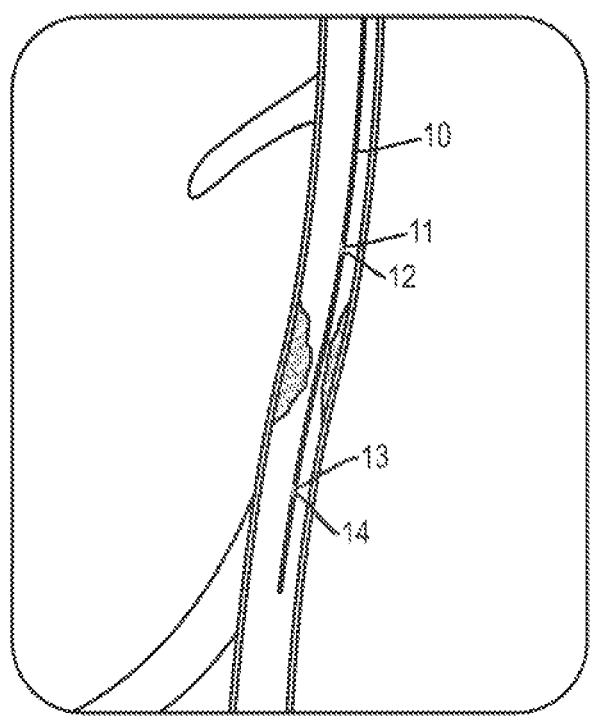
FIGS. 6-9 illustrate conceptually separate coronary artery scenarios in which the disclosed guidewire, disposed relative to a coronary stenosis, may be used to improve diagnosis, in accordance with the disclosure.

FIG. 5 illustrates conceptually the electrogram characteristics from normal healthy myocardium ischemic viable myocardium and nonviable myocardium. In healthy heart tissue, both pairs of electrodes should record nearly identical electrograms. If the pair of electrodes distal to a coronary stenosis records an electrogram that is different from the electrogram recorded by the pair of electrodes proximal of the stenosis, is characterized by the bottom signal, this is an indication of ischemia and that the occlusion is clinically relevant.

FIGS. 6-9 illustrate conceptually a guidewire 10 with two pairs of closely space electrodes, separated by a short distance, with three separate coronary artery scenarios in which the disclosed guidewire may be used to improve diagnosis. In all three scenarios, a Fractional Flow Reserve (FFR) value is estimated to be in the range of between 0.75 to 0.85 and considered borderline. The disclosed guidewire 10 and technique provide added diagnostic information needed to make the appropriate decision on the need to perform a PTCA or stenting procedure as set forth in greater detail herein.

Figure 7:
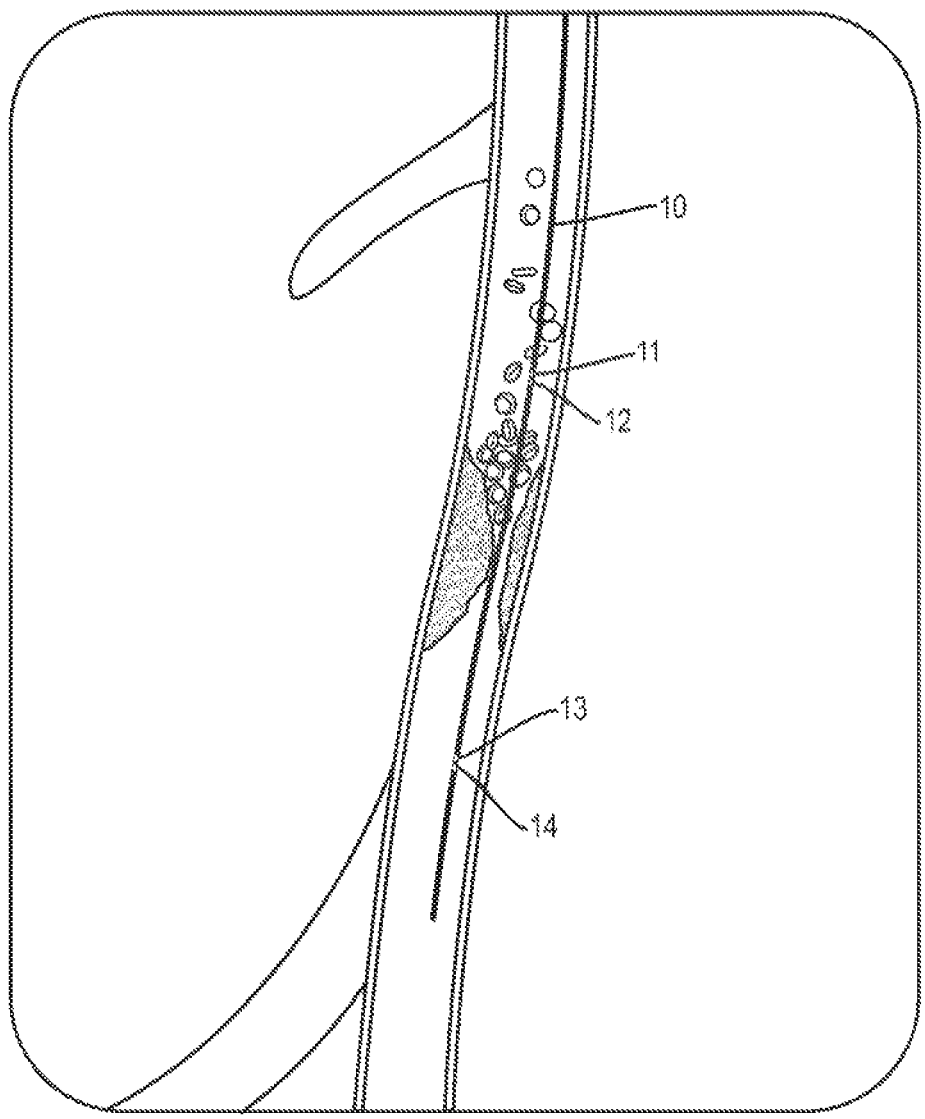

In FIG. 7, the illustrated coronary stenosis is clinically significant based on the FAME trial results and should be stented. An attempt to pace the heart distal of the stenosis is unsuccessful and therefore there is no clinical need to stent. There is no benefit to opening this vessel as the tissue is "dead" (non-viable).

Figure 8:
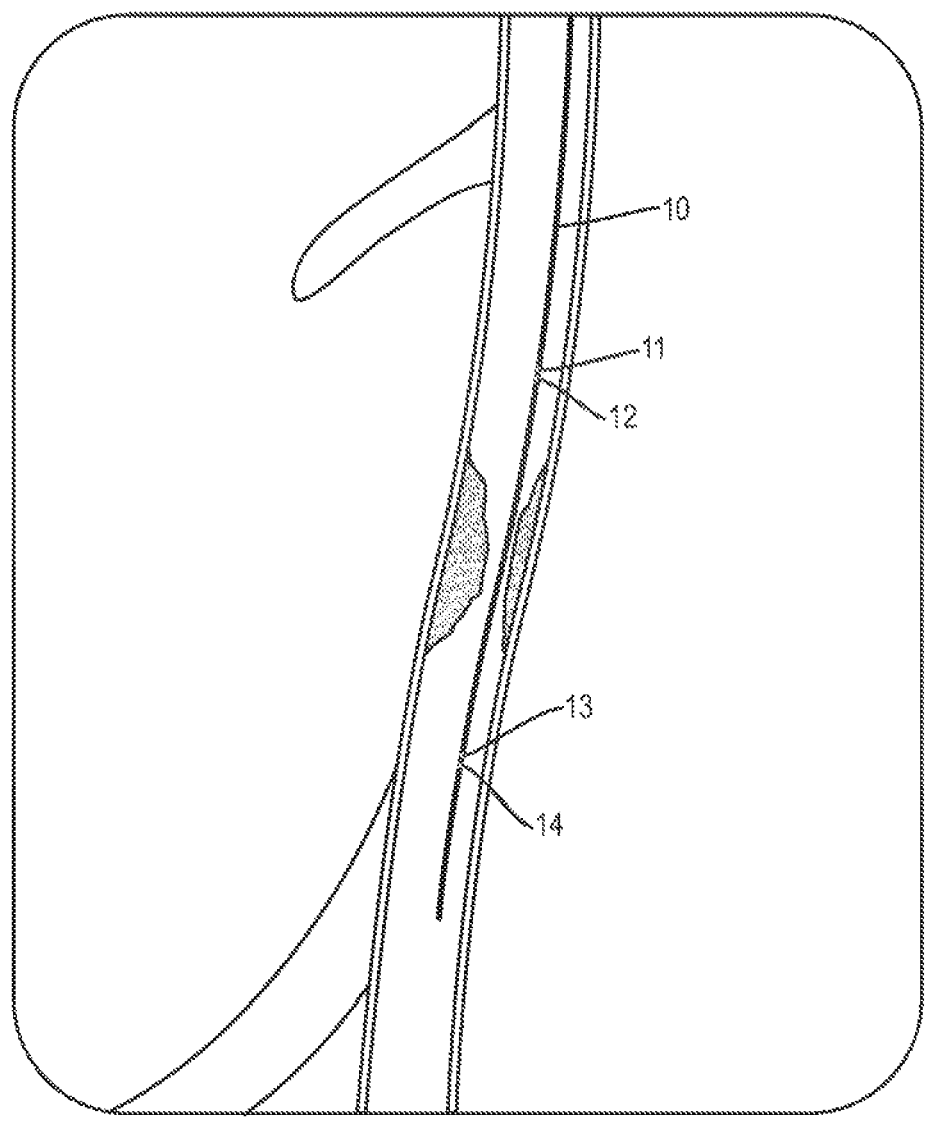

In FIG. 8, the patient has multi-vessel stenoses. Is this the vessel causing the patient's symptoms? The stenosis is of borderline significance based on the FAME trial. Assessment of ICEG distal to the stenosis during drug induced stress or pacing induced stress shows no ischemia. Patient's symptoms therefore are likely caused by another blockage.

Figure 9:
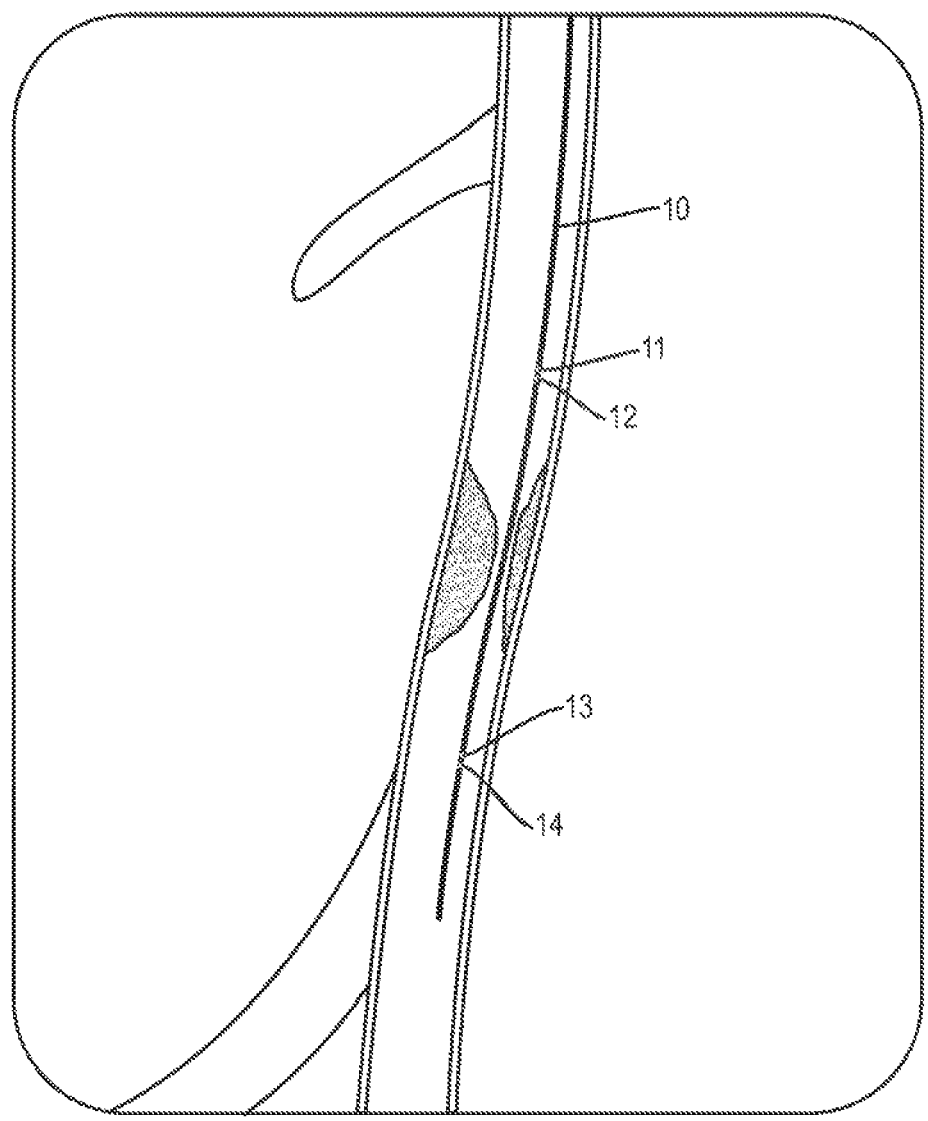

In FIG. 9, the stenosis is borderline insignificant based on the FAME trial. FFR value for this stenosis is borderline and may not need stenting. To stent or not to stent? Assessment of ICEG distal to the occlusion using the guidewire and techniques disclosed herein during drug induced stress or pacing induced stress shows ischemia, and, therefore, this vessel should be stented.

In one embodiment, in the setting of a chronic total occlusion, the apparatus and techniques disclosed herein may be utilized for determining viability of the vessel tissue by inserting the disclosed guidewire into a parallel neighboring artery or into the corresponding coronary vein (which runs parallel to the artery) which may be accessed via the coronary sinus and utilizing the measurements and analyses described herein.

In one embodiment, a table of values, measured in Ohms or fractions of Ohms, representing the resistive values of different types of obstructive materials, e.g. Hardened atherosclerotic plaque, soft atherosclerotic plaque or other types of plaque, etc., found within coronary arteries may be used in conjunction with the measured average impedance of the un-occluded coronary artery, e.g. as an offset or scaler value, to derive in near real time a customized comparative impedance to which the measured average impedance of an occluded coronary artery can be compared to further provide a practitioner with a potential indication of the nature of the hardness of the occlusive material within the artery as well as the degree of stenosis or minimal lumen diameter, in addition to the other measurements disclosed herein. It is anticipated that the following type of atherosclerotic plaque compositions would have different impedances:

Cholesterol

Lipid rich plaque

Inflammatory (unstable) plaque

Calcified plaque

Neointimal proliferation (typical of a restenotic plaque post PCI)

Plaque containing a stent (a metallic stent will have a low impedance)

Empirically derived impedance values representing such type of atherosclerotic plaque compositions may be stored in a table or other data structure associated with the measurement circuit module 16 to which the disclosed guidewire is electrically coupled. Impedance signals measured by the disclosed guidewire may be compared directly with the stored values, or with a calibrated or reference value, and, once the characteristic impedance signature of one of the foregoing plaque types is detected, such determination may be utilized in a procedure for not only determining the necessity of stenting the vessel but in follow-up procedures as well.

In one embodiment, following a PTCA or stenting procedure, the processes and guidewire disclosed herein may be used to measure the average impedance of the unobstructed and/or stented coronary artery to determine if the procedure was successful. Such post-procedural measurements may be performed at various time intervals following the PTCA or stenting procedure, e.g. 3 months, 6 months, 12 months, 24 months, etc., to aid in the determination of whether the procedure was successful or needs to be repeated.

According to other aspects of the disclosure, the disclosed multi-electrode guidewire 10 has three or more pairs of electrodes any pair of which may be selectively activated or deactivated in accordance with signal switching configurations programmable in measurement circuit module 16 in order to accommodate lesions or stenosis of varying lengths so that it is possible to have a pair of electrodes positioned both proximal and distal of a stenosis within the vessel of the living being. Such a plurality of electrode pairs may also be utilized to address patients with multiple tandem (serial) stenoses in a given vessel.

According to other aspects of the disclosure, the disclosed multi-electrode guidewire 10 has only one pair of electrodes carried in the distal region of the guide catheter.

According to another aspect of the disclosure, low pressure inflation, e.g. to 2 ATM (subangioplasty pressure), of a compliant measuring balloon may be used to confirm impedance across a lesion in conjunction with the techniques described herein. The balloon material, and, therefore, also its insulated saline content, is non-conducting (very high impedance), allowing for assessing the difference in impedance when balloon is not inflated (blood with low impedance) and when the balloon is inflated to 2 ATM (vessel wall around the balloon—higher impedance than blood) from electrodes proximal to the lesion to electrodes distal to the lesion. The results of the impedance measurement with the balloon in situ can then be compared with the impedance measurements taken with the guidewire for possible corroboration of the size of the stenosis According to yet another aspect of the disclosure, the techniques described herein may be utilized with a low pressure measuring balloon to assess diameter of reference vessel diameter to guide selection of stent size and the stenosis diameter—by assessing the volume of contrast required at low pressure to occlude the vessel. Occlusion of the vessel can be tested by contrast injection or by measuring the point of abrupt rise in electrical impedance along the vessel.

Although the illustrative embodiments described herein have been described with reference to use with coronary artery stenosis, the disclosed guidewire and techniques may be equally applicable to other vascular organs, including peripheral arterial disease, e.g. leg muscle ischemia, or cerebral arterial disease (cerebral EEG signal ischemia), as well as with vessels within other organs of the body.

According to another aspect of the disclosure, guidewire 10 may be utilized to transmit mechanical or acoustic vibrations from the distal tip region thereof to a proximal sensor located, for example, at either the hub of vascular valved introducer or even attached as a clip on mechanical coupling to the guidewire, in both cases the sensor being external to the patient. In one embodiment, a table of numeric values representing vibratory or acoustic signatures of different types of obstructive materials, e.g. hardened atherosclerotic plaque, soft atherosclerotic plaque or other types of plaque, etc., found within coronary arteries may be stored directly in the sensor itself or in memory associated with measurement circuitry module 16 and compared to the vibratory or acoustic signal detected by the sensor and identified to a practitioner, if enough similarities exist, to further provide with a potential indication of the nature of the hardness of the occlusive material within the artery as well as the degree of stenosis or minimal lumen diameter, in addition to the other measurements disclosed herein.

According to other aspects of the disclosure, the disclosed multi-electrode guidewire 10 has utility in addition to those methods described previously. For example, the disclosed multi-electrode guidewire 10 may be used in coronary arteries and/or coronary veins to guide electrophysiology and ablation procedures in patients with cardiac arrhythmias.

The disclosed multi-electrode guidewire 10 may be used to guide delivery of stem cell or myocardial regenerative therapy or local drug delivery in patients with heart failure or arrhythmias.

The disclosed multi-electrode guidewire 10 may be used to localize+/−stimulate ganglionated plexi of the autonomic nervous system of the heart in patients with cardiac arrhythmias, heart failure, or patients with vasospastic (Prinzmetal) angina.

The disclosed multi-electrode guidewire 10 may be used to guide cardiac resynchronization therapy.

The disclosed multi-electrode guidewire 10 may be used to guide non-cardiac procedures including neuro-interventional procedures for vascular disease but also for epilepsy, tumor, stroke, tremor, Parkinson's disease.

The disclosed multi-electrode guidewire 10 may be used deliver ablative radiofrequency or electric energy to cause deliberate occlusion of a coronary artery or coronary vein or to cause ablation/cauterization of neighboring myocardium, as well is to cerebral vessels and the brain.

The disclosed multi-electrode guidewire 10 may be used to sense temperature, e.g. through incorporation of a thermistor or thermocouple. It can be anticipated that non-viable and viable but hibernating (stunned) myocardium to be metabolically inactive and therefore the blood in the local artery and local coronary vein to be cooler. It can be anticipated that vulnerable unstable thin capped atherosclerotic plaque with inflammation to have a different temperature than other neighboring intima of the coronary artery.

The disclosed multi-electrode guidewire 10 may be used to change the temperature of coronary arterial venous blood, such as for raising the temperature, via resistive heating of the proximal electrodes, and sensing time to detection of change in temperature in the distal electrodes as a reflection of coronary blood flow.

The disclosed multi-electrode guidewire 10 may be used to cool, via a Peltier effect, the blood in a coronary artery or vein or cerebral artery or vein in order to pre-condition and to reduce reperfusion injury in the setting of acute myocardial infarction and in the setting of acute stroke.

The disclosed multi-electrode guidewire 10 may be used to perform electro-location, that is the detection of a change in electric field gradient, whereby the distal most electrode 14 and proximal most electrode 11 have a charge there between or across them and the middle two electrodes 12 and 13 detect changes in field strength. As the guidewire 10 is advanced or pulled back across a lesion/stenosis the impact of atherosclerotic plaque compared to blood in the vessel lumen is detectable by a change in electric field strength/gradient.

The disclosed multi-electrode guidewire 10 may be used to deliberately induce ischemia. More specifically, the pair of electrodes 11, 12 proximal to the stenosis may be used to pace the heart rapidly, e.g. at 120-160 bpm for a period of time, e.g. one minute, to deliberately induce ischemia. The electrogram evidence of ischemia in the distal pair of electrodes may then be assessed both during pacing from the proximal pair of electrodes and immediately after pacing stops, e.g. first 15 seconds thereafter. Evidence of ischemia in the electrograms detected from the distal electrode pair 13, 14 during induced ischemia can then be examined.

According to other aspects of the disclosure, multiple guide wires, similar to guidewire 10, have combined utility in addition to those methods described previously. For example, deploying two separate multi-electrode guidewires simultaneously where by one guidewire remains in the main (coronary) vessel and the second wire is advanced as a roving/scout wire into (coronary) side branches. By using a combination of the electrodes in two separate guidewires a 3-dimensional (3D) map can be generated. Such a 3-D map, if color coded according to one or more parameters, can display the distribution and extent of myocardial ischemia or of non-viability, dead scar tissue. Such a 3-D map may visualize not only area but also 3-D volumetric display of the full myocardial wall thickness from the epicardium to the endocardium, e.g. by using septal side branches. Such a map can be generated by use of impedance or electromagnetic or electric or other energy or signal or data. Such a 3-D map can be generated with the use of external or body surface emitters or receivers or electrodes, or, alternatively can be generated by use of the combination of the electrodes on the intravascular guidewires exclusively, or, alternatively can be generated by use of one or a multiplicity of electrodes incorporated into a guiding catheter. A 3-D map can also be generated by a single multi-electrode guidewire, i.e. without the need for deployment of a second guidewire, whereby one guidewire is used to advance distally and to rove into side branches.

Figure 4B:
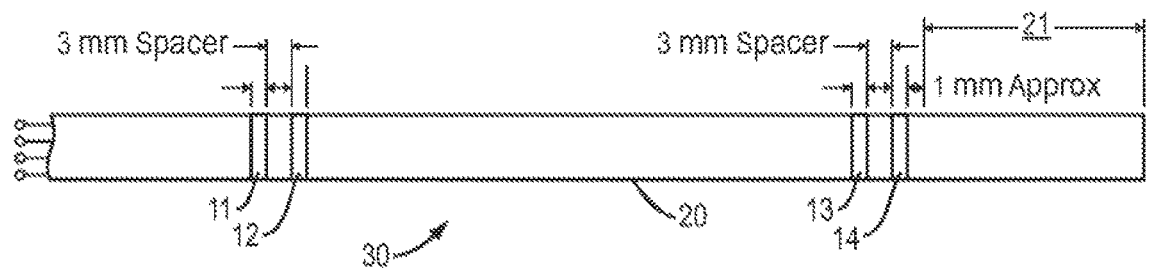
FIG. 4B illustrates conceptually a guide catheter in accordance with the disclosure.

According to another aspect of the disclosure, one or more electrode pairs similar to those described herein with reference to guidewire 10 may be disposed on a coronary guiding catheter 30 in the distal region thereof, as illustrated in FIG. 4B. The electrodes can not only be placed proximate the distal tip of the guiding catheter which would be in the ostium of the coronary artery but also could be placed more proximally in the aorta to provide a wider 3-D reference range for triangulation of the position of the multi-electrode guidewire, such as disclosed herein.

Figure 4C:
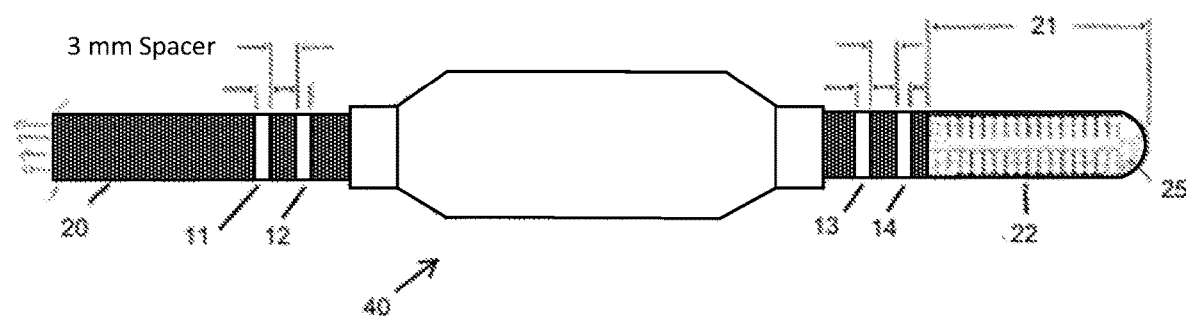
FIG. 4C illustrates conceptually a partial cutaway view of a balloon catheter in accordance with the disclosure.

According to another aspect of the disclosure, one or more electrode pairs similar to those described herein with reference to guidewire 10 may be disposed on a catheter having a dilatory mechanism such as the steerable balloon angioplasty catheter 40, illustrated in FIG. 4C. With balloon angioplasty catheter 40, the closely spaced pair of electrodes and can be carried on the catheter shaft, which may be similar to tube 20, both proximal and distal of a dilatation balloon or other device used to increase the diameter of a stenosis vessel. Note, catheter designs with other dilatory mechanisms, such as ablation catheters or atherectomy catheters, with or without a dilatory balloon, may be implemented with electrode pairs both proximal and distal of the dilatory mechanism in the distal region thereof to achieve similar functionality as the guidewire 10 disclosed herein.

It will be appreciated that any of the described aspects, features and options described in view of the disclosed methods apply equally to the system, measurement circuit module and guidewire device. It will be understood that any one or more of the described aspects, features and options as described herein can be combined. For purposes of clarity and a concise description, features are described herein as part of the same or separate embodiments, however, it will be appreciated that scope of the concepts may include embodiments having combinations of all or some of the features described herein.

It will be obvious to those reasonably skilled in the art that modifications to the apparatus and process disclosed here in may occur, including substitution of various components or values, without parting from the true spirit and scope of the disclosure.

What is claimed is:

1. An intravascular device comprising:
   an elongate tubular body configured to be positioned within a vessel of a patient, the elongate tubular body having a distal end region; and
   one or more pairs of electrodes disposed on an exterior surface of the elongate tubular body proximate the distal end region and spaced thereapart by a measurement distance, wherein the one or more pairs of electrodes are configured to be communicatively coupled a measurement circuit configured to process signal data received from the one or more pairs of electrodes, determine a change in the measurement distance between the one or more pairs of electrodes during a cardiac cycle, and determine functional characteristics of a myocardium subtended by the vessel based on the change in measurement distance over the cardiac cycle.

2. The intravascular device of claim 1, wherein the one or more pairs of electrodes comprise a first pair of electrodes and a second pair of electrodes, wherein a spacing between the first pair and a spacing between the second pair and the measurement distance define a set ratio.

3. The intravascular device of claim 2, wherein the set ratio is in the range between 7:1 to 25:1.

4. The intravascular device of claim 2, wherein the set ratio is in the range between 12:1 to 18:1.

5. The intravascular device of claim 2, wherein the measurement circuit is further configured to measure an impedance between the first pair of electrodes and the second pair of electrodes.

6. The intravascular device of claim 2, wherein the measurement distance enables the first pair of electrodes and the second pair of electrodes to be positioned on different sides of a stenosis through which the elongate tubular body is disposed within a vessel.

7. The intravascular device of claim 2, further comprising a third pair of electrodes spaced axially along the elongate tubular body from the first pair of electrodes and the second pair of electrodes.

8. The intravascular device of claim 2, wherein the first pair of electrodes and the second pair of electrodes are configured to sense electrical signals from living tissue adjacent to the electrodes.

9. The intravascular device of claim 2, wherein the first pair of electrodes and the second pair of electrodes are electrically coupled together.

10. The intravascular device of claim 1, wherein the elongate tubular body is an intravascular wire.

11. The intravascular device of claim 1, wherein the elongate tubular body is a catheter.

12. A system comprising:
    an intravascular device comprising:
       elongate tubular body configured to be positioned within a vessel of a patient, the elongate tubular body having a distal end region, and
       one or more pairs of electrodes disposed on an exterior surface of the elongate tubular body proximate the distal end region and spaced thereapart by a measurement distance;
    a signal source operably coupled to the one or more pairs of electrodes; and
    a measurement circuit operably coupled to the one or more pairs of electrodes and configured to:
       receive signal data received from the one or more pairs of electrodes,
       determine a change in the measurement distance between the one or more pairs of electrodes during a cardiac cycle, and
       determine functional characteristics of a myocardium subtended by the vessel based on the change in measurement distance over the cardiac cycle.

13. The intravascular device of claim 1, wherein the functional characteristics comprise data characterizing a viability of the myocardium subtended by the vessel.

14. The system of claim 12, wherein the functional characteristics comprise data characterizing a viability of the myocardium subtended by the vessel.

* * * * *